(12) United States Patent
Luce (10) Patent No.: US 7,771,353 B2
(45) Date of Patent: Aug. 10, 2010

(54) METHOD AND APPARATUS FOR TEAR FILM MEASUREMENT

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 693 days.

(21) Appl. No.: 11/279,269

(22) Filed: Apr. 11, 2006

(65) Prior Publication Data

US 2007/0237715 A1    Oct. 11, 2007

(51) Int. Cl.
*A61B 3/16*    (2006.01)
(52) U.S. Cl. .................................. 600/398; 351/200
(58) Field of Classification Search .............. 600/398; 351/200
See application file for complete search history.

(56) References Cited

U.S. PATENT DOCUMENTS

| | | | |
|---|---|---|---|
| 5,865,742 A * | 2/1999 | Massie | 600/405 |
| 6,875,175 B2 * | 4/2005 | Luce | 600/398 |
| 2003/0092979 A1 * | 5/2003 | Luce et al. | 600/398 |
| 2004/0002640 A1 | 1/2004 | Luce | |
| 2006/0109423 A1 * | 5/2006 | Wang | 351/206 |

FOREIGN PATENT DOCUMENTS

| | | | |
|---|---|---|---|
| CA | 2553711 A1 | 7/2005 | |
| WO | 2005/058151 A1 | 6/2005 | |
| WO | 2005058151 A1 | 6/2005 | |
| WO | 2006/031909 A2 | 3/2006 | |
| WO | 2006031909 A2 | 3/2006 | |

OTHER PUBLICATIONS

Little, et al. "Environmental Influences on Hydrogel Lens Dehydration and hte Postlens Tear Film", Jul. 1995, ICLC vol. 22, pp. 148-152.*

Himebaugh, et al., Use of Retroillumination to Visualize Optical Aberrations Caused by Tear Film Break-up, School of Optometry, Indiana University, Bloomington, IN, 15 pages.

(Continued)

*Primary Examiner*—Max Hindenburg
*Assistant Examiner*—Renee Danega
(74) *Attorney, Agent, or Firm*—Hodgson Russ LLP (57) ABSTRACT

Tear film is measured without contacting the eye by comparing reflectance from the eye when the tear film is undisturbed with reflectance from the eye when the when the tear film is disturbed. If the reflectance levels differ somewhat, it is an indication that a healthy tear film exhibiting good specular reflection was present initially and was disturbed by the air pulse. However, if the reflectance levels are close to one another, it is an indication that a less-than-normal tear film was present initially (dry eye). In a described embodiment, tear film is disturbed by an air pulse directed at the eye, and a photosensitive detector is positioned to receive light from an illumination beam after the beam is reflected by the eye to generate a reflectance signal. The reflectance signal is evaluated to calculate a tear film index.

9 Claims, 5 Drawing Sheets

OTHER PUBLICATIONS

Townsend, et al, Individualize dry eye treatment regimens for each patient, Primary Care Optometry News, Nov. 2005, vol. 10, No. 11, 3 pages.

Wang, J. et al.: "Precorneal and Pre- and Postlens Tear Film Thickness Measured Indirectly with Optical Coherence Tomography", Investigative Ophthalmology & Visual Science, vol. 44, No. 6, Jun. 2003, pp. 2524-2528, Association for Research in Vision and Ophthalmology, US.

Yokoi, N., et al.: Reflective meniscometry: a non-invasive method to measure tear meniscus curvature, British Journal of Ophthamology, 1999, No. 83, pp. 92-97.

Wang, J., et al.: Precorneal and Pre- and Postlens Tear Film Thickness Measured Indirectly with Optical Coherence Tomography, Investigative Ophthalmology & Visual Science, Jun. 2003, vol. 44, No. 6, pp. 2524-2528.

* cited by examiner

METHOD AND APPARATUS FOR TEAR FILM MEASUREMENT

FIELD OF THE INVENTION

The present invention relates generally to the field of ophthalmology, and more particularly to a method and apparatus for quickly and non-invasively measuring tear film of an eye.

BACKGROUND OF THE INVENTION

Dry eye syndrome ("dry eye" for short) refers to any one or more deficiencies of the tear film which coats the surfaces of the cornea and conjunctiva of the eye. The tear film is a layer of substances secreted by glands around the eye and is intended to keep the eye surfaces constantly lubricated. The tear film protects the corneal tissue, keeps the eye comfortable, provides proteins and nutrients for the eye, and refracts light. Thus, dry eye generally involves discomfort, pain, poor vision, and/or eye injury. Common symptoms described by patients include scratchiness or grittiness, sensation of a foreign body in the eye, aching, burning, fatigue, contact lens discomfort, excess mucus discharge, sensitivity to light, sensitivity to smoke, and blurred vision.

Most clinicians diagnose and treat dry eye based on the symptoms alone. For example, the patient may fill out a questionnaire that is scored according to a point scale or otherwise evaluated by the clinician to determine whether a diagnosis of dry eye is indicated. This subjective methodology fails to provide objective evidence of tear film deficiency.

Various tests have been developed to measure tear film and determine tear film deficiency in a more objective manner. One such test is the Schirmer test, which is intended to measure the amount of tears that are produced by the eye. If the tears are collected for some time, for example five minutes or so, then one can determine whether the amount produced is sufficient for maintaining eye health. If total tear production is below normal, this is evidence of dry eye. If total tear production is normal or above normal, but there are still symptoms of ocular discomfort, then evaporative dry eye, for example due to blepharitis or Rosacea, may be present. In the Schirmer test, a 35 mm×5 mm size filter paper strip is used to measure the amount of tears that are produced over a period of five minutes. The strip is placed at the junction of the middle and lateral thirds of the lower eye lid, and is conducted tinder ambient light. The patient is instructed to look forward and to blink normally during the course of the test. A negative test (more than 10 mm wetting of the filter paper in five minutes) means the patient produces a normal amount of tears. Patients with dry eye have wetting values of less than 5 mm in five minutes. An important limitation of the Schirmer test is that there may be considerable variability in the results of tests done at different times and by different doctors. So, although this is perhaps the most common dry eye test performed, its main utility may really be in diagnosing patients with severe dry eye. Sequential tests to follow the course of a patient with mild dry eye may not be of value. Moreover, there is one point of some debate in the Schirmer test. When an anesthetic eyedrop is not used, then this test is thought to measure the basal tear secretion plus the reflex tear secretion. When an anesthetic eyedrop is used, then this test is thought to measure only the basal tear secretion. There is compelling reason to believe that the tears measured by these two different methods may not sufficiently differentiate between basal and reflex tear production. Most clinicians perform this test after using anesthetic eyedrops to numb the eye. However, The National Eye Institute workshop on dry eyes recommended not to use anesthetic eyedrops before performing this test. The cutoff value is similar whether or not anesthetic is used. To measure the reflex tear secretion, the Schirmer II test may be performed. The Schirmer II test is performed by irritating the nasal mucosa with a cotton-tipped applicator prior to measuring tear production.

Many clinicians regard the Schirmer test as unduly invasive and of little value for mild to moderate dry eyes. Other less invasive methods to assess the adequacy of tear production have been developed. The phenol red thread test is one such test and is commercially available under the trademark ZONE-QUICK®. A cotton thread impregnated with phenol red dye is used; phenol red is pH sensitive and changes from yellow to red when wetted by tears. A crimped end of a 70 mm long thread is placed in the lower conjunctival fornix. After fifteen seconds, the length of the color change on the thread—indicating the length of the thread wetted by the tears—is measured in millimeters. Wetting lengths should normally be between 9 mm and 20 mm. Patients with dry eye have wetting values of less than 9 mm.

Another test is the tear breakup time (BUT) test. Normal tear film is continuous, and blinking maintains the tear film continuity. If the eye is kept open long enough, without blinking, the tear film will start to break up. As a result, the eye will feel uncomfortable causing the patient to blink. In patients with dry eye the tear film is unstable, and breaks up faster. Therefore, the tear break up time in patients who have dry eyes is shorter. Said in another way, if the patient's tear break up time is relatively short then the patient may have dry eye. Fluorescein break up time (FBUT) is used most commonly. A strip of fluorescein is applied in the lower eyelid fornix and then removed. The patient is asked to blink three times and then look straight forward, without blinking. The tear film is observed under cobalt-blue filtered light of the slitlamp microscope and the time that elapses between the last blink and appearance of the first break in the tear film is recorded with a stopwatch (a break is seen as a dark spot in a sea of blue). FBUT of ten seconds or less is consistent with dry eye. FBUT has important limitations. For example, touching the filter paper strip to the conjunctiva can stimulate reflex tearing. Although special fluorescein strips designed specifically for FBUT are available and are claimed to deliver a fixed microvolume of fluorescein without stimulating reflex tearing, the mere presence of fluorescein in the tears perhaps also changes the tear film properties, so FBUT measurements may not be truly physiological.

To overcome these limitations, non-invasive break up time (NIBUT) methods have been developed. They are called non-invasive because the eye is not touched. Instruments such as a keratometer, hand-held keratoscope or tearscope are required to measure NIBUT. A prerupture phase that precedes actual break up of the tear film can also be observed with some techniques. This pre-rupture phase is termed tear thinning time (TTT). Measurement is achieved by observing the distortion (TTT) and/or break up (NIBUT) of a keratometer mire (the reflected image of keratometer grid). The clinician focuses and views the crisp mires, and then records the time taken for the mire image to distort (TTT) and/or break up (NIBUT). NIBUT measurements are longer than fluorescein break up time. NIBUT values of less than 15 seconds are consistent with dry eye. TTT and NIBUT are considered to be more patient-friendly, repeatable and precise than the methods discussed above, but like the other methods they are time consuming and require skill to administer.

Thus, a need exists for a diagnostic tool capable of quickly and objectively measuring tear film without significant discomfort to the patient, and without the need for significant skill and practice on the part of the person administering the test.

SUMMARY OF THE INVENTION

It is therefore an objective of the present invention to provide a method and apparatus for measuring tear film of a patient in a non-invasive manner.

It is another objective of the present invention to provide a method and apparatus for measuring tear film of a patient instantaneously.

It is a further objective of the present invention to provide a method and apparatus for measuring tear film that yields a quantitative measurement value in the form of a tear film index.

It is a further objective of the present invention to provide a method and apparatus for measuring tear film that does not require a high level of skill and practice on the part of the person making the measurement.

It is a further objective of the present invention to provide a method and apparatus for measuring tear film that may be implemented as a software upgrade to an existing ophthalmic instrument, without need for additional hardware.

These and other objectives of the present invention are met by an apparatus and method whereby reflectance from the eye is used to measure tear film.

A method for measuring tear film in accordance with the present invention generally comprises the steps of measuring a first reflectance value associated with the eye when the tear film is in an undisturbed state, disturbing the tear film, measuring a second reflectance value associated with the eye when the tear film is in a disturbed state, and comparing the first reflectance value to the second reflectance value. If the first and second reflectance values differ somewhat, it is an indication that a healthy tear film exhibiting good specular reflection was present initially and was disturbed by the air pulse. However, if the two values are close to one another, it is an indication that a less-than-normal tear film was present initially (dry eye) giving rise to some scattering from the epithelium, and disturbance of such tear film does not significantly change the observed reflectance. A difference between the first and second reflectance values may be calculated and reported as a tear film index. The tear film may be disturbed by directing an air pulse at the eye, and reflectance may be observed by directing an illumination beam at the eye and locating a photosensitive detector to receive light reflected by the eye to generate a reflectance signal.

An apparatus for measuring tear film in accordance with the present invention generally comprises a source emitting light for reflection by the eye, a photosensitive detector arranged to receive light reflected by the eye and generate a reflectance signal indicative of the intensity of the received light, means for disturbing the tear film of the eye, and processing means for comparing the reflectance signal generated when the tear film is in an undisturbed state to the reflectance signal generated when the tear film is in a disturbed state caused by the means for disturbing the tear film. In a described embodiment the means for disturbing the eye includes a motor-driven piston and cylinder for generating an air pulse discharged through a tube directed toward the eye. The processing means preferably calculates a tear film index that may be reported on a display and stored in memory.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
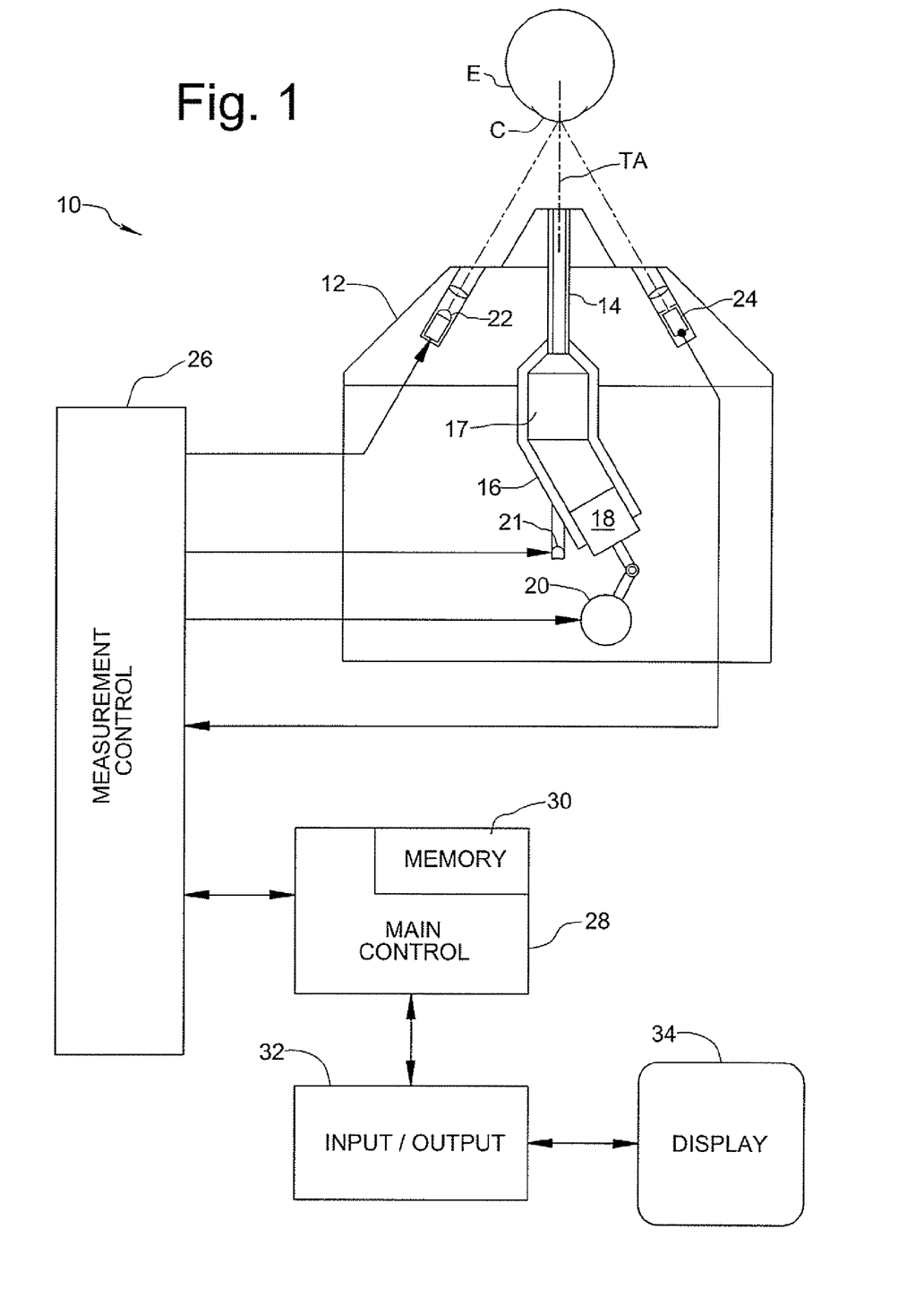
FIG. 1 is a schematic view of a tear film measurement apparatus formed in accordance with an embodiment of the present invention.

FIG. 1 shows a tear film measurement apparatus 10 formed in accordance with an embodiment of the present invention, in schematic view. A test portion of apparatus 10 is alignable with a patient's eye E and includes a nosepiece 12 in which an air discharge tube 14 is fixed to direct an air pulse along test axis TA to the cornea C of eye E. The air discharge tube 14 is in communication with a plenum chamber 17 defined by a cylinder body 16, and a piston 18 is axially movable within cylinder body 16 under force supplied by a motor 20 to rapidly increase pressure within plenum chamber 17, thereby causing an air pulse to be discharged from the air discharge tube 14 toward cornea C. Motor 20 is connected to a measurement controller 26, which supplies a drive signal for energizing the motor. A fixation target 21, such as an LED or other light source, is arranged along test axis TA and connected to measurement controller 26 to receive an illumination signal from the measurement controller. While the present embodiment uses a piston-cylinder arrangement to generate an air pulse for disturbing the tear film, gases other than air may be used, and other means of disturbing the tear film may be employed, including an ultrasonic transducer.

The test portion further includes a light source 22 arranged to one side of test axis TA for directing an oblique illumination beam to cornea C in response to an illumination signal from measurement controller 26 to which light source 22 is connected. Preferably, light source 22 emits light in the infrared spectral range so as not to cause a visual response by the patient. A photosensitive detector 24 is arranged on the opposite side of test axis TA from light source 22 to receive illumination light that is reflected by cornea C. Detector 24 generates a reflectance signal indicative of the intensity of light received by the detector. The reflectance signal information is inputted to measurement controller 26 to which detector 24 is connected. Other locations of discharge tube 14, light source 22, and detector 24 are possible, the important aspect being that a region of the tear film can be disturbed, and the reflectance associated with such region can be observed.

In accordance with the present invention, the reflectance signal corresponding to an undisturbed condition of the tear film is compared to the reflectance signal corresponding to a disturbed condition of the tear film to provide a quantitative tear film index (TFI) as a measurement output.

When the tear film is undisturbed, it forms a thin layer over cornea C. Light reaching detector 24 is reflected essentially entirely from the front surface of the tear film, and is characterized as dielectric reflection caused by the difference in index of refraction between air and the tear film. A normal tear film provides an optically smooth surface due to the surface tension of the tear fluid (primarily water) despite the fact that the underlying corneal tissue—the epithelium—is optically rough relative to the tear film surface. See, for example, Nikole L. Himebaugh, O D, et al., "Use of Retroillumination to Visualize Optical Aberrations Caused by Tear Film Break-Up," *Optometry and Vision Science*, vol. 80(1), pages 69-78 (January 2003). The normal reflection from the undisturbed tear film surface is commonly referred to as a specular reflection, in that it preserves image quality. However, when the tear film is disturbed by removing or seriously compromising the tear film, then the light impinging on the eye is scattered by the exposed epithelium, which is optically rough. The scattering reduces the light reaching detector 24, thereby reducing the generated reflectance signal.

With continued reference to FIG. 1, the reflectance signal information generated by detector 24 is processed by measurement controller 26 and by a main controller 28 of apparatus 10 that is connected to measurement controller 26. The signal processing electronics provided by measurement controller 26 and main controller 28 includes filters for eliminating signal noise and an analog-to-digital converter for digitizing the reflectance signal information. Accordingly, the amplitude of the reflectance signal is expressed in FIGS. 2 and 3 as a digital "count" value of arbitrary units. Main controller 28 includes or is linked to memory, generally designated as 30, which may include EPROM, SRAM, and DRAM modules as well as other storage devices in communication with main controller 28. A display 34 is connected to main controller 28 through input/output electronics 32 for displaying measurement results as will be described below.

Those skilled in the art of ophthalmic instruments will recognized that various structural elements of the tear film measurement apparatus 10 may be found in commercially available non-contact tonometers used to measure intraocular pressure. It is therefore possible to make apparatus 10 by adding programming code to an existing non-contact tonometer for evaluating the reflectance signal information generated thereby. Currently, the reflectance signal information generated by a non-contact tonometer is processed to determine a moment in time when corneal applanation occurs, so that a corresponding plenum pressure can be determined (see for example, the peaks in FIGS. 2 and 3). By adding software for evaluating other portions of the reflectance signal in accordance with the present invention, a non-contact tonometer may be upgraded to provide tear film measurement capability with relative ease. Such an upgrade may be made, for example, in an AT-555 Non-Contact Tonometer manufactured by Reichert, Inc. Of course, apparatus 10 of the present invention may be manufactured as a stand alone instrument as well.

Figure 2:
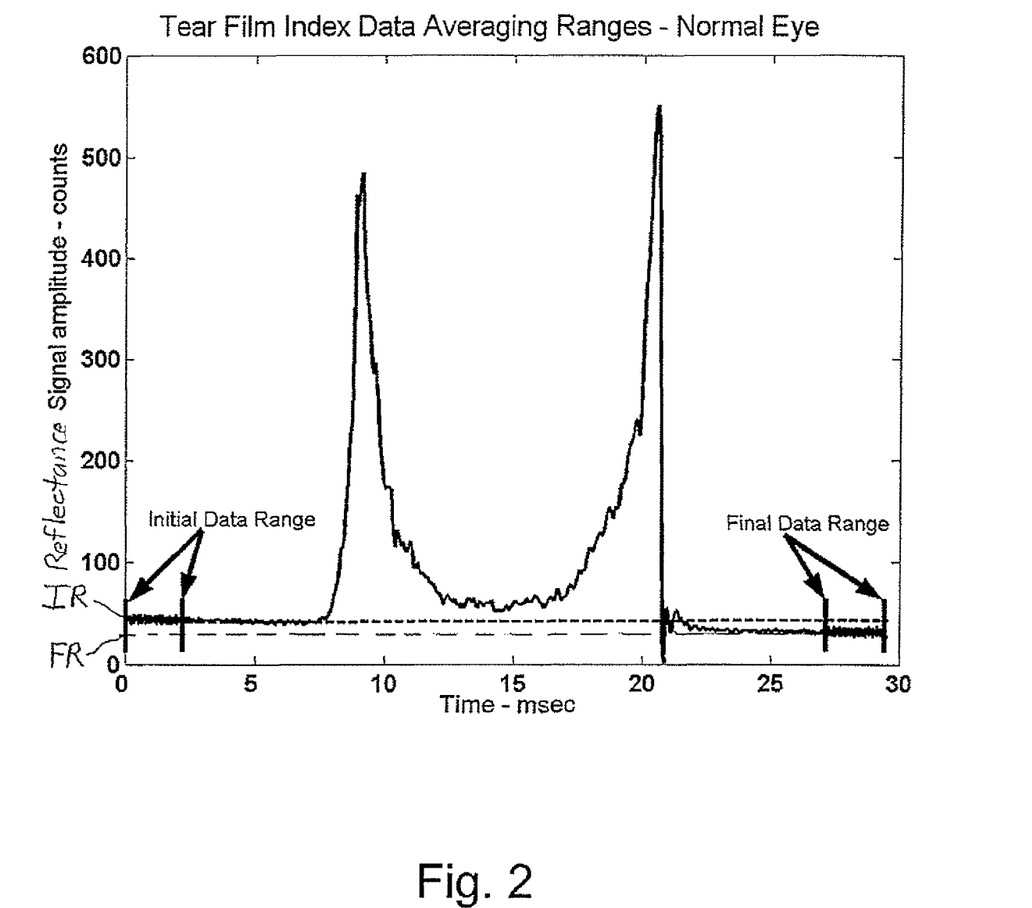
FIG. 2 is a plot showing a reflectance signal generated during a measurement cycle by the measurement apparatus, wherein the measured eye has a normal tear film.
Figure 3:
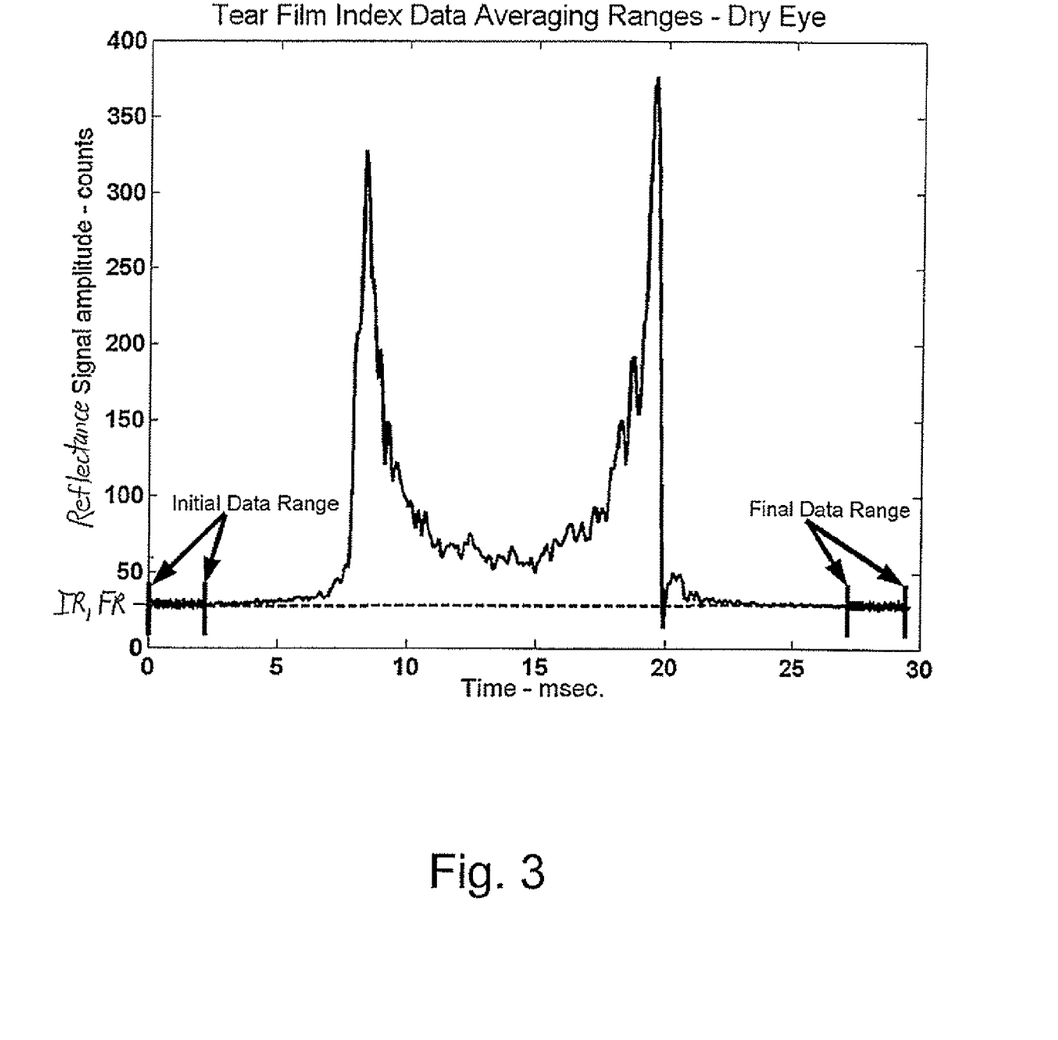
FIG. 3 is a plot similar to that of FIG. 2, except wherein the measured eye is characterized as having dry eye syndrome.

In the present embodiment, the tear film is disturbed by an air pulse discharged from air discharge tube 14. The force of the air pulse reduces the tear film in a central circular region of the cornea about three millimeters in diameter. The illumination beam from light source 22 is directed at this region, and detector 24 observes reflectance from this region. FIGS. 2 and 3 show plots of the reflectance signal generated by detector 24 as a function of time during air pulse generation for an eye having a normal tear film and an eye characterized as having dry eye, respectively. As may be seen in FIG. 2, there is an initial time period before the air pulse reaches the eye, and a "final" time period immediately after application of the air pulse to the eye. During the initial time period, the tear film is undisturbed. During the final time period, the tear film is in a disturbed condition, having been reduced by the force of the air pulse. In accordance with the present invention, reflectance signal data are sampled during the initial time period and the final time period, and a comparison of the sampled reflectance signal data is made, as will be described in detail below with reference to FIG. 5. It will be understood that the final time period must be selected such that it elapses prior to a blink response by the patient, which normally occurs at about 65 msec or 70 msec, because the blink response may substantially restore the tear film. During a period between the initial time period and the final time period, the reflectance signal exhibits a pair of peaks which correspond to inward and outward flattening or "applanation" of the corneal surface caused by the air pulse, which results in more coherent reflection than the natural curved surface of the cornea; these peaks are not of interest with respect to the present invention, except as an indicator of air pulse timing. In this regard, the air pulse need not be strong enough to flatten the cornea, but merely strong enough to reduce the tear film in a region of interest.

Figure 4:
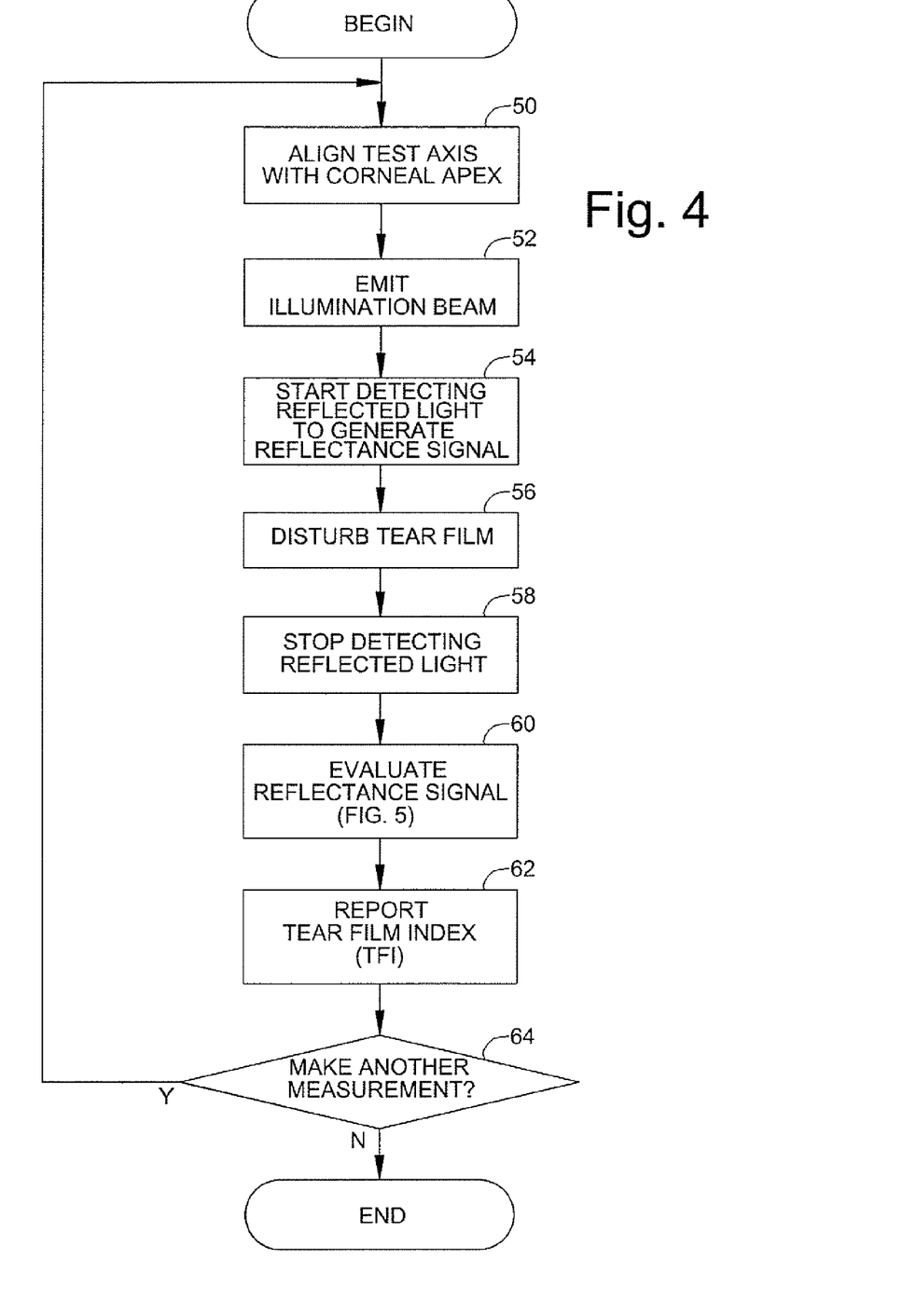
FIG. 4 is a flow chart of a method for measuring tear film in accordance with an embodiment of the present invention.

FIG. 4 generally illustrates process flow for measuring tear film in accordance with an embodiment of the present invention. Initially, in block 50, test axis TA is aligned with the apex of cornea C as the patient gazes at target 21. Different alignment conditions may be applicable depending upon the means used to disturb the cornea and the arrangement of such means with respect to light source 22 and detector 24. Once alignment is achieved, light source 22 is energized by measurement controller 26 to emit an illumination beam toward the eye pursuant to block 52. Light source 22 remains energized throughout the measurement process, and the reflected light is detected in block 54 by detector 24 to generate a reflectance signal throughout the measurement process. In block 56, the tear film is disturbed, such as by energizing motor 20 to force piston 18 in a direction causing an air pulse to be discharged from air discharge tube 14 toward the eye. At some point in time, preferably after blink response by the patient, light source 22 may be shut off and detection of reflected light discontinued as indicated in block 58. In block 60, the reflectance signal information generated by detector 24 is processed and evaluated as described below to calculate a tear film index (TFI), which is reported in block 62, such as by display 34, a printout, or other form of output. The measured TFI is also stored in memory 30. If another measurement is desired, query 64 returns flow to block 50 to repeat the measurement procedure.

Regarding measurement protocol and repetition, it is recognized that the first time a measurement is made on a patient, the tear film that is measured is the result of tear film production over an extended period of time. Making more than one measurement in a short period of time (seconds apart) measures a tear film resulting from short term replenishment because after each measurement there is an automatic blink response which "recoats" the eye with tear fluid. It is quite likely that the best procedure will exploit the short term tear replenishment situation, rather than just an initial measurement. It is expected that measurement results may be more reproducible on a second or later measurement(s).

Figure 5:
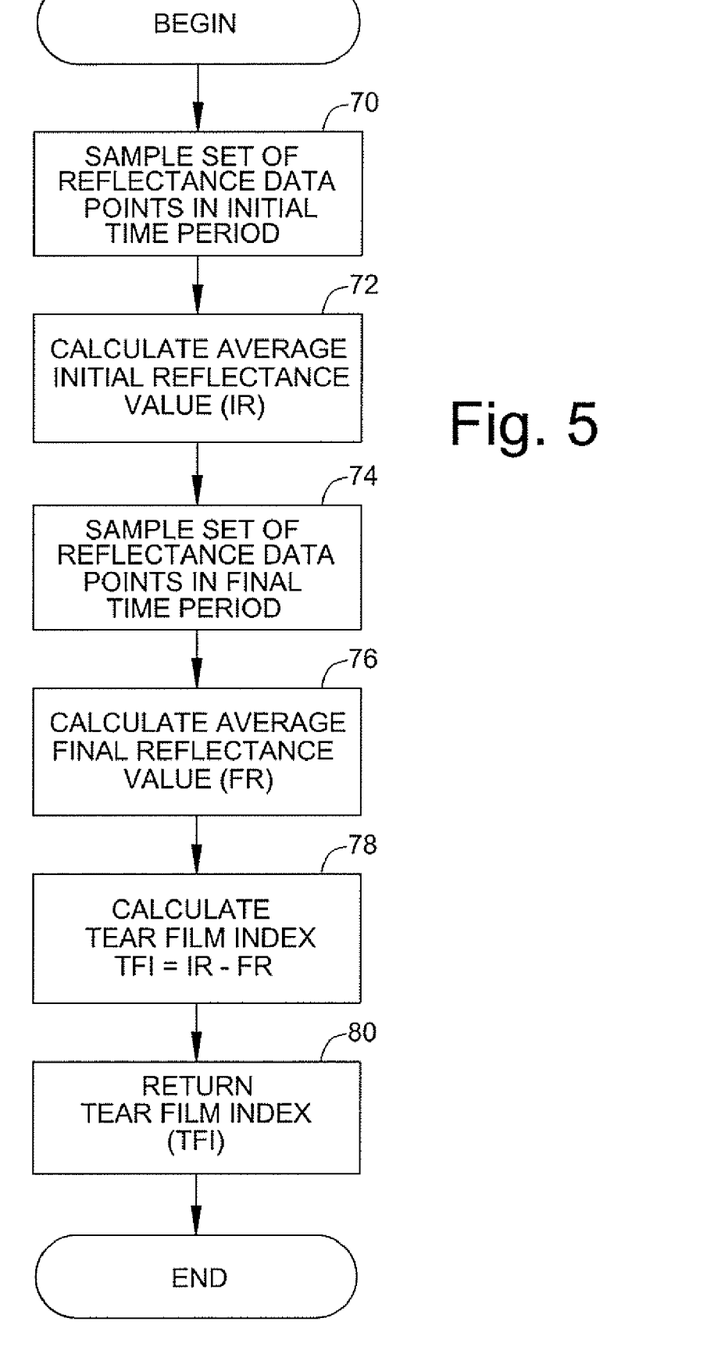
FIG. 5 is a flow chart illustrating signal evaluation steps used to calculate a tear film index from an acquired reflectance signal in accordance with an embodiment of the present invention.

A methodology for evaluating the reflectance signal to calculate TFI will now be described in detail with reference to FIG. 5. The methodology is better understood in physical terms by additional reference to FIGS. 2 and 3 showing reflectance signals associated with a normal eye (FIG. 2) and a dry eye (FIG. 3). First, in block 70, the digitized reflectance signal information is sampled at regular intervals during an initial time period corresponding to an undisturbed state of the tear film. In FIGS. 2 and 3, the initial time period spans approximately from time t=0 to time t=2.25 msec, during which period the reflectance signal is sampled every 75 μsec to provide a set of thirty data points in the initial time period. Then, in block 72, an average initial reflectance value (IR) is calculated from the sampled data points. Similar steps are then taken in blocks 74 and 76 to sample the digitized reflectance signal information at regular intervals during a final time period corresponding to a disturbed state of the tear film, and calculate an average final reflectance value (FR) from the sampled data points corresponding to the disturbed tear film state. In FIGS. 2 and 3, the final time period spans approximately from time t=27 msec to time t=29.25 msec, during which period the reflectance signal is sampled every 75 μsec to provide a set of thirty data points in the final time period. As mentioned above, the final time period is well before the onset of a blink response by the patient, which normally occurs at 65 to 70 msec. In accordance with the present invention, the initial reflectance value IR and the final reflectance value FR are compared to each other to provide a measurement of the tear film. If the two values differ somewhat, it is an indication that a healthy tear film providing good specular reflection was present initially and was disturbed by the air pulse. By contrast, if the two values are close to one another, it is an indication that a less-than-normal tear film was present initially (dry eye) giving rise to some scattering from the epithelium, and disturbance of such tear film does not significantly change the observed reflectance. According to an embodiment of the present invention, and as indicated in block 78, a tear film index (TFI) is calculated as

TFI=IR−FR where TFI is tear film index, IR is the initial reflectance value, and FR is the final reflectance value. The calculated tear film index TFI is then returned as a measurement result in block 80.

Initial trial measurements on a test population of eyes show that the tear film index TFI is a positive number approximately 98% of the time. The reflectance signals shown in FIG. 2 (normal eye) and FIG. 3 (dry eye) illustrate typical observations. In FIG. 2, there is a decrease from initial reflectance IR to final reflectance FR. However, in FIG. 3, the initial reflectance IR and the final reflectance FR are substantially the same. By examining distribution of the tear film index for a statistically significant population of eyes, as well as other information relating to dry eye symptoms in the test population, it is possible to establish a threshold TFI value at or below which an eye is considered to have dry eye syndrome.

While the present invention described above has been described in terms of an "initial" time period and a "final" time period, it is emphasized that it is not the sequence of the time periods that is important, but rather the state of the tear film during those time periods. Thus, it is conceivable that a measurement process could be devised that measures reflectance during a disturbed tear film state prior to measuring reflectance during an undisturbed tear film state, and such a process is within the boundaries of the present invention.

PARTS LIST

10 Apparatus for measuring tear film
12 Nosepiece
14 Discharge tube
16 Cylinder body
17 Plenum chamber
18 Piston
20 Motor
21 Fixation target
22 Light source
24 Photosensitive detector
26 Measurement controller
28 Main controller
30 Memory
32 Input/output electronics
34 Display
50-80 Flow chart blocks

What is claimed is:

1. A method of measuring a tear film of an eye comprising the steps of:
    A) measuring a first reflectance value associated with the eye when the tear film is in an undisturbed state;
    B) disturbing the tear film by directing a fluid pulse at the tear film, wherein force exerted by the fluid pulse on the tear film reduces a region of the tear film;
    C) measuring a second reflectance value associated with the eye when the tear film is in a disturbed state caused by the fluid pulse and prior to restoration of the tear film by a blink reflex in response to the fluid pulse; and
    D) comparing the first reflectance value to the second reflectance value.

2. The method according to claim 1, wherein the first reflectance value and the second reflectance value are measured by illuminating a region of the eye with a beam of light and detecting light reflected by the eye.

3. The method according to claim 2, wherein the beam of light is an infra-red beam.

4. The method according to claim 2, wherein the beam of light has a diameter of approximately three millimeters.

5. The method according to claim 2, wherein the light reflected by the eye is detected to provide reflectance signal information, and the reflectance signal information is sampled for an initial time period corresponding to the undisturbed state of the tear film and for a final time period corresponding to the disturbed state of the tear film.

6. The method according to claim 5, wherein the first reflectance value is an average reflectance value over the initial time period, and the second reflectance value is an average reflectance value over the final time period.

7. The method according to claim 1, wherein the step of comparing the first reflectance value to the second reflectance value includes calculating a difference between the first reflectance value and the second reflectance value.

8. The method according to claim 7, wherein the difference is calculated by subtracting the second reflectance value from the first reflectance value.

9. The method according to claim 8, further comprising the step of reporting the difference as a quantitative tear film index.

* * * * *